US011662600B2

(12) United States Patent
Leube et al.

(10) Patent No.: US 11,662,600 B2
(45) Date of Patent: May 30, 2023

(54) DEVICE, METHOD AND COMPUTER PROGRAM FOR PRODUCING TWO POINT LIGHT SOURCES OF THE SAME WAVELENGTH ON A PUPIL PLANE OF AN EYE AND FOR DETERMINING A NEURAL TRANSFER FUNCTION OF A VISUAL PATHWAY

(71) Applicant: Carl Zeiss Vision International GmbH, Aalen (DE)

(72) Inventors: Alexander Leube, Aalen (DE); Nikolai Suchkov, Kusterdingen (DE); Christina Schwarz, Kusterdingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/053,145

(22) Filed: Nov. 7, 2022

(65) Prior Publication Data
US 2023/0090748 A1     Mar. 23, 2023

Related U.S. Application Data

(63) Continuation of application No. PCT/EP2021/062126, filed on May 7, 2021.

(30) Foreign Application Priority Data

May 8, 2020  (DE) .................... 10 2020 205 851.2

(51) Int. Cl.
*G02B 27/48*     (2006.01)
*G03B 21/20*     (2006.01)
*G02B 26/08*     (2006.01)

(52) U.S. Cl.
CPC ......... *G02B 27/48* (2013.01); *G03B 21/2033* (2013.01); *G02B 26/0816* (2013.01)

(58) Field of Classification Search
CPC . G02B 27/48; G02B 26/0816; G03B 21/2033
See application file for complete search history.

(56) References Cited

U.S. PATENT DOCUMENTS 5,396,303 A    3/1995 Peters et al.
5,579,161 A   11/1996 Nobutoshi
(Continued)

FOREIGN PATENT DOCUMENTS

CN    102335088 A    2/2012
DE   102008041458 B4  11/2012
(Continued)

OTHER PUBLICATIONS

Williams, "Aliasing in Human Foveal Vision," Vision Research, Elsevier Ltd., US, vol. 25, No. 2, pp. 195-205, 1985.
(Continued)

*Primary Examiner* — Thomas A Hollweg
*Assistant Examiner* — Mary A El-Shammaa
(74) *Attorney, Agent, or Firm* — Tautz & Schuhmacher LLC; Georg Hasselmann

(57) ABSTRACT

A device, a method, and a computer program for producing two point light sources of the same wavelength on a pupil plane of an eye of a user are disclosed, as well as a device, a method, and a computer program for determining a neural transfer function of the visual pathway of the user. The device for determining the neural transfer function includes a coherent light source for generating a light beam; an optical device for separating the light beam into sub-light beams, superpositioning the respective sub-light beams, and adjusting contrast and spatial phase in an interference pattern; and a beam path for guiding the superposed sub-light (Continued)

beams such that two point light sources of the same wavelength are produced. The devices are compact and robust, allow a variable presentation of different interference patterns, and can thus be easily operated in a commercial product in a clinical setting.

11 Claims, 3 Drawing Sheets

(56) References Cited

U.S. PATENT DOCUMENTS

| | | | | |
|---|---|---|---|---|
| 7,973,936 B2* | 7/2011 | Dantus | ................. | G01J 11/00 356/451 |
| 2008/0309873 A1 | 12/2008 | Levecq et al. | | |
| 2019/0129278 A1* | 5/2019 | Ichihara | ................. | G02F 1/365 |
| 2021/0325652 A1* | 10/2021 | Tang | ................. | G02B 21/367 |

FOREIGN PATENT DOCUMENTS

| WO | WO-2020036619 A1 * | 2/2020 | ............. G02B 1/002 |
|---|---|---|---|
| WO | WO-2021224454 A1 * | 11/2021 | |
| WO | WO-2021259982 A1 * | 12/2021 | |

OTHER PUBLICATIONS

Sekiguchi et al., "Aberration-free measurements of the visibility of isoluminant gratings," Journal of the Optical Society of America A, Optica Publishing Group, US, vol. 10 No. 10, pp. 2105-2117, 1993.

Williams et al., "Double-pass and interferometric measures of the optical quality of the eye", Journal of the Optical Society of America A, Optica Publishing Group, US, vol. 11, No. 12, pp. 3123-3135, 1994.

Mon-Williams et al., "Improving vision: neural compensation for optical defocus", The Royal Society, London, UK, vol. 265, No. 1390, pp. 71-77, Jan. 7, 1998.

Castillo et al., "Exploring the Stiles-Crawford effect of the first kind with coherent light and dual Maxwellian sources", Applied Optics, Optica Publishing Group, US, vol. 52, No. 1, pp. A1-A8, 2013.

International Search Report issued in PCT/EP2021/062126, to which this application claims priority, dated Jul. 28, 2021, and English-language translation thereof.

Written Opinion issued in PCT/EP2021/062126, to which this application claims priority, dated Jul. 28, 2021.

International Preliminary Report on Patentability issued in PCT/EP2021/062126, to which this application claims priority, completed Jul. 29, 2022, and English-language translation thereof.

* cited by examiner

DEVICE, METHOD AND COMPUTER PROGRAM FOR PRODUCING TWO POINT LIGHT SOURCES OF THE SAME WAVELENGTH ON A PUPIL PLANE OF AN EYE AND FOR DETERMINING A NEURAL TRANSFER FUNCTION OF A VISUAL PATHWAY

CROSS REFERENCE TO RELATED APPLICATIONS

This application is a continuation application of international patent application PCT/EP2021/062126, filed May 7, 2021, designating the United States and claiming priority to German patent application DE 10 2020 205 851.2 filed on May 8, 2020, both of which are hereby incorporated by reference in their entireties.

TECHNICAL FIELD

The present disclosure relates to an apparatus, a method, and a computer program for producing two point light sources of the same wavelength on a pupil plane of at least one eye of a user, and an apparatus comprising these, and a method related thereto, and a computer program for determining a neural transfer function of a visual pathway of the user.

BACKGROUND

Human vision is a complex procedure, which can be subdivided into an optical contribution, a modulation transfer function, and a neural transfer function. In this context, the neural transfer function of a visual pathway of a user describes a neuronal contribution to human vision. The term "visual pathway" in this case denotes a chain of organs configured to enable a user to see, with the chain of organs comprising at least an eye, a retina, an optic nerve and all centers in the brain that contribute to vision. The "visual pathway" is also referred to as "visual system". The neural transfer function therefore represents the main factor for behavior-related contrast perception within the scope of vision. Knowledge of the neural transfer function allows optical treatments by means of spectacles, spectacle lenses, contact lenses, intraocular lenses, and/or refractive surgery to be adapted to a selected user. Further, the neural transfer function can be used as a diagnostic tool for neuronal disorders and for the teaching of perception.

The related art has disclosed apparatuses and methods for determining the neural transfer function of the visual pathway of a user, which are based on an analytic method or on an interferometric method. The analytic methods comprise a separate measurement of the liquor and of the modulation transfer function, whereupon the neural transfer function is determined analytically by means of mathematical models. However, the analytic methods were found to be time-consuming and inaccurate.

DE 10 2008 041 458 B4 discloses a method for determining the neural contrast sensitivity function of an eye, including the following method steps:
 a) determining the optical contrast sensitivity function of the eye;
 b) determining the physiological contrast sensitivity function of the eye;
 c) calculating the neural contrast sensitivity function of the eye by division from the previously determined optical and physiological contrast sensitivity functions of the eye, with the optical contrast sensitivity function of the eye being calculated from averaging a plurality of previously determined optical contrast sensitivity functions and/or the physiological contrast sensitivity function (CSF) of the eye being calculated from averaging a plurality of previously determined physiological contrast sensitivity functions and/or the neural contrast sensitivity function of the eye being calculated from averaging a plurality of previously calculated neural contrast sensitivity functions of the eye.

M. Mon-Williams, J. R. Tresilian, N. C. Strang, P. Kochhar and J. P. Wann, *Improving vision: neural compensation for optical defocus*, Proc. R. Soc. Lond. B 265, 1998, pp. 71-77, describe a significant improvement in the capability of recognizing letters after the eyes of a user were not subjected to a refractive correction for a relatively long period of time. To this end, the optical contrast sensitivity function of the eye of each subject was initially measured in a first experiment. Then, the physiological contrast sensitivity function of the eye was detected in a second experiment, and a comprehensive evaluation was subsequently carried out.

The interferometric methods use two coherent light beams which are projected into the eye of the user and which interfere in the retina of the eye. To this end, the light beam is usually controlled mechanically, and this limits the speed and the efficiency of an associated apparatus which, on account of a complicated beam path, has reduced stability and robustness. Especially on account of their susceptibility to vibrations, such apparatuses cannot be used in a clinical environment or in a commercial product. Moreover, an adjustment of contrasts in the interference fringes requires an optical auxiliary element, making the structure of the apparatus even more complex. The known apparatuses can therefore only be operated by a person skilled in the art of ray optics.

D. R. Williams, *Aliasing in Human Foveal Vision*, Vision Res. 25(2), 1985, pp. 195-205, describes a laser interferometer which enables contrast sensitivity measurements that are largely uninfluenced by optical defocus in the eye. A beam splitter splits light from a laser into two light beams arranged in mirror-image fashion relative to one another. Each light beam impinges on an acousto-optic modulator, which can be used to adjust contrast and spatial phase of the interference fringes. A spatial filter which is introduced into the respective beam path and comprises a microscope objective and an aperture stop removes spatial noise from each light beam and in each case expands the latter. A respective combination of two optical lenses and one mirror collimates the respective expanded light beam and in each case produces an image representation of the relevant aperture stop within a glass cube. The two light beams cross in the glass cube while propagating in almost opposite directions, as a result of which it is possible to adjust a spatial frequency of the interference fringes. A further combination of in each case a mirror and a collimating lens guides the two light beams back to the beam splitter, where they are merged and subsequently impinge on a field stop, which images the interference fringes onto the retina of the eye. It is possible to focus the field stop by adjusting a distance between the field stop and a further lens; alternatively, a further beam splitter can be used to this end. A linear polarizer is situated directly in front of the eye and is configured to remove depolarized stray light in order to avoid a reduction in the contrast of the interference rings. A vibration-damped optical table, folded beam paths, and secure coupling between the mirrors and beam splitters are proposed for the purposes of reducing vibrations.

N. Sekiguchi, D. R. Williams and D. H. Brainardt, *Aberration-free measurements of the visibility of isoluminant gratings*, J. Opt. Soc. Am. A 10 (10), 1993, pp. 2105-2117, describe an apparatus comprising two identical laser interferometers, wherein each of the two laser interferometers is configured to produce interference fringes on the retina of the eye of the user, with it being possible to adjust a relative phase between the interference fringes produced by the two laser interferometers. In this case, too, each laser interferometer comprises two acousto-optic modulators, by means of which it is possible to adjust the contrast and the spatial phase of the interference rings, a spatial filter comprising a microscope objective and an aperture stop, and a field stop which images the interference fringes onto the retina of the eye.

US 2008/0309873 A1 discloses a method for correcting aberrations of the eye, applied to an ophthalmological instrument which operates with an analysis light beam, comprising: measuring aberrations of the eye which interfere with the analysis beam, correcting the phase of the wavefront of the analysis beam as a function of the measured values of the aberrations, measuring eye movements independently of the measurement of the aberrations, and modifying the correction of the phase of the wavefront of the analysis beam as a function of the measurement of the eye movements.

Williams, David R., et al., *Double-pass and interferometric measures of the optical quality of the eye*, JOSA A, 1994, vol. 11, no. 12, pp. 3123-3135, compares two methods for measuring the modulation transfer function (MTF) of the human eye, an interferometric method and a double-pass method. The same observer, the same state of refraction, the same pupil size (3 mm) and the same wavelength (632.8 nm) were used for both methods. A close correspondence was found in the double-pass method between the plane of the subjectively best focus for the observer and the plane of the objectively best focus, indicating that a majority of the reflected light during the double pass is restricted to the individual cones by the receptor layer. MTFs produced in the double-pass method had a loss in the modulation transfer, which can probably be traced back to the light reflected by the choroid.

Sara Castillo and Brian Vohnsen, *Exploring the Stiles-Crawford effect of the first kind with coherent light and dual Maxwellian sources*, Applied Optics, 2013, Vol. 52, No. 1 describe that the visual effect of light incident on the retina in oblique fashion is reduced by the Stiles-Crawford effect of the first kind. This is normally analyzed by virtue of scanning a small Maxwellian source over the pupil of the eye while subjective visibility comparisons are made with a static reference field that enters the eye near the pupil center. The publication proposes an alternative characterization method with two coherent Maxwellian point sources, which are located on opposite sides of the pupil. This leads to interference fringes on the retina with an underlying phase gradient. The wavefront inclination on the retina can be adjusted by changing the power ratio of the two point sources. This allows the Stiles-Crawford effect of the first kind to be examined without the incident light being scanned over the pupil. To this end, use was made of a spatial light modulator with holographic phase maps, in order to produce two Maxwellian point sources on the pupil, which project a certain phase variation onto the retina.

SUMMARY

In particular in relation to the background by N. Sekiguchi, see above, it is an object of the present disclosure to provide an apparatus, a method, and a computer program for producing two point light sources of the same wavelength on a pupil plane of at least one eye of a user, and an apparatus, a method, and a computer program for determining a neural transfer function of a visual pathway of the user, which at least partly overcome the listed disadvantages and restrictions of the related art.

In particular, the apparatuses should have a compact and robust structure, and thus allow simple operation in order to be able to be used in a commercial product in a clinical environment.

This object is achieved by an apparatus, a method, and a computer program for producing at least two point light sources of the same wavelength on a pupil plane, or on the respective pupil plane, of at least one eye of a user and by an apparatus, a method, and a computer program for determining a neural transfer function of a visual pathway of the user, having at least one coherent light source includes at least one polychromatic light source with a supercontinuum laser source and at least one tunable wavelength filter. Typical configurations, which can be realized individually or in combination, are presented in the exemplary embodiments below.

Hereinafter the terms "exhibit," "have," "comprise," or "include," or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B," "A has B," "A comprises B," or "A includes B" can refer both to the situation in which no further element aside from B is provided in A, that is to say to a situation in which A consists exclusively of B, and to the situation in which, in addition to B, one or more further elements are provided in A, for example element C, elements C and D, or even further elements.

In a first aspect, the present disclosure relates to an apparatus for producing at least two point light sources of the same wavelength on a pupil plane, or on the respective pupil plane, of at least one eye of a user. As is well known, the term "point light source" denotes a light source of negligible extent in relation to its distance from the illuminated object. In the case of the present disclosure, at least the two point light sources of the same wavelength are produced on a pupil plane, or on the respective pupil plane, of at least one eye of a user. Instead of the term "user" used here, one of the terms "subject," "spectacle wearer," "wearer," or "subject" can also be used synonymously. In this context, the term "pupil plane" relates to a plane which can be placed through the entrance opening of the eyeball, referred to as a "pupil," and which is restricted by a circumference of the pupil. Furthermore, within the scope of the present disclosure, the term "retina" denotes a photosensitive layer which is located on the background of the eyeball and typically extends from an edge of the pupil to where the optic nerve leaves.

The apparatus for producing at least two point light sources of the same wavelength on a pupil plane, or on the respective pupil plane, of at least one eye of a user comprises:
- at least one coherent light source for producing at least one light beam;
- at least one optical device for splitting the at least one light beam into two pairs of partial light beams respectively, for superposing the respective partial light beams in each pair, and for adjusting contrast and spatial phase in at least one interference pattern formed for each pair from the superposition of the two partial light beams; and
- at least one beam path for guiding each pair of the superposed partial light beams such that at least two point light sources of the same wavelength are produced on a pupil plane, or on the respective pupil plane, of at least one eye of a user;

wherein the at least one optical device comprises at least one digital light modulation element.

The present apparatus for producing at least two point light sources of the same wavelength on a pupil plane, or on the respective pupil plane, of at least one eye of a user comprises at least one coherent light source which is configured to produce at least one light beam. The term "coherent light source" denotes a light source configured to produce coherent light which propagates in the form of light beams which are guided along a defined beam path within the apparatus. In this case, the light beams emitted by the light source have a temporally stable phase relationship among themselves, as a result of which a temporally stable interference is enabled between the light beams or partial light beams branched off therefrom. In this context, the term "interference" denotes a superposition of two light beams or partial light beams which, in the case of coherent light, form a temporally stable interference pattern, in particular in the form of interference fringes arranged parallel to one another in one or two dimensions, the interference fringes typically having a fixed period. Such a two-dimensional pattern may be selected from a checkerboard pattern; and/or from alternating structures which may comprise rings or lines in particular; and/or from attenuating structures.

In principle, any coherent light source, in particular at least one laser, is suitable for the at least one light source here. Typically, the at least one coherent light source is at least one monochromatic light source, more particularly at least one monochromatic laser light source, which provides coherent light within a narrowband range serving to produce at least the two point light sources of the same wavelength on the respective pupil plane of the at least one eye of the user. Alternatively, use can be made of at least one polychromatic light source, more particularly at least one supercontinuum laser source. Laser light is referred to as "supercontinuum" if it has a broadband optical spectrum able to comprise a frequency range of at least one octave following the passage through a nonlinear optical medium. As explained in more detail below, the use of at least one supercontinuum laser source advantageously allows a provision of coherent laser light at a plurality of wavelengths, with the apparatus being able to additionally comprise at least one wavelength filter, typically at least one tunable wavelength filter, which is configured to select a narrowband range from the broadband range. In this context, a combination of the at least one supercontinuum laser source and the at least one tunable wavelength filter may enable a fast determination of the neural transfer function over the entire visible spectrum or a part thereof.

The present apparatus for producing at least two point light sources of the same wavelength on a pupil plane, or on the respective pupil plane, of at least one eye of a user furthermore comprises an optical device configured to
- split the light beam into at least two pairs of partial light beams;
- superpose the respective partial light beams in each pair; and
- adjust contrast and spatial phase in an interference pattern formed for each pair from the superposition of the two partial light beams.

In this case, the term "partial light beam" denotes a light beam which is produced by an incident light beam as a consequence of passing through an optical element configured to this end, while the term "split" relates to a division of the incident light beam into at least two partial light beams. In the case of the present disclosure, at least one incident light beam is split such that at least two pairs of partial light beams are formed, with each pair comprising two individual partial light beams which, after passing over a portion of the beam path, are superposed on one another again. On account of the coherent nature of the individual partial light beams, an interference pattern is formed from the superposition of the two partial light beams in each pair, as explained in more detail above and below, the interference pattern being able to be present, in particular, in the form of interference fringes arranged parallel to one another or in the form of a checkerboard pattern. In this context, the term "superposition" relates to a guidance of the two partial light beams in each pair such that the separately guided partial light beams ultimately meet again at the same location in the beam path in order to thus form a superposition of their amplitudes. In this context, the optical device is configured such that contrast and spatial phase in interference patterns formed for each pair are adjustable.

While such optical devices known from the related art comprise a plurality of optical components, in particular a plurality of beam splitters, acousto-optic modulators, glass cubes, mirrors and lenses which are arranged in positions precisely aligned with respect to one another, the disclosure proposes the use of at least one digital light modulation element as optical device. In this case, the term "digital light modulation element" denotes an optical apparatus which comprises a multiplicity of individually controllable optical elements that are configured to modulate an incident light beam.

The at least one digital light modulation element can typically comprise at least one spatial light modulator or at least one digital micromirror device. The term "spatial light modulator" (abbreviated "SLM") denotes an optical device configured to impress an intensity pattern, in particular in the form of a spatial modulation and/or a phase, on an incident light beam, the intensity pattern being able to be impressed electronically and/or optically. For this reason, the spatial light modulator is usually suitable for pulse shaping and/or production of optical gratings. As a rule, the digital micromirror device (abbreviated "DMD") is used to modulate a digital image onto a light beam. To this end, the digital micromirror device comprises an arrangement comprising a multiplicity of tiltable micromirrors which have an edge length of the order of micrometers and are arranged in a matrix, with each micromirror being able to be individually adjustable by means of electrostatic fields. An incident light beam is decomposed into individual pixels as a result of this arrangement and then reflected pixelwise. However, other types of digital light modulation elements are possible.

Within the scope of the disclosure present here, the at least one digital light modulation element can typically be configured to adjust the contrast and the spatial phase in an interference pattern formed for each pair from the superposition of the two partial light beams. In particular, as mentioned below, it is possible to adjust the respective contrast of the interference pattern, especially the interference fringes or the two-dimensional pattern, by defining a relationship between the areas of two pupils, which corresponds on the at least one digital light modulation element to rings assigned to the respective pair of partial light beams. Typically, the at least one digital light modulation element may be configured to this end to carry out an isoluminant adjustment of the contrast in the interference pattern formed for each pair by virtue of the areas of the two rings assigned to the respective pair of partial light beams being chosen to be of equal size on the at least one digital light modulation element. As an alternative or in addition, the adjustment of the contrast in the interference pattern formed for each pair can be implemented by means of a change in a modulation depth, wherein a first-order diffraction efficiency can be reduced, typically for one pupil. Such a procedure allows contrast changes in the respective interference patterns to be carried out at a repetition rate of the at least one digital light modulation element, for example at 10 Hz to 100 Hz, typically at 25 Hz to 50 Hz, in particular at 30 Hz, while a luminance of the two partial light beams can be kept constant at the same time. The term "luminance" denotes an areal brightness, with which the at least one eye of a user can perceive an illuminated surface.

Within the scope of the disclosure present here, the at least one digital light modulation element can typically be configured to implement a lateral displacement of the partial light beams of one of the pairs of partial light beams in relation to a propagation direction of the partial light beams of one of the other pairs of partial light beams. In this way, the at least one digital light modulation element can split an incident coherent light beam into two pairs of partial light beams that are inclined symmetrically with respect to one another. As explained in more detail below, it is possible in the process to define at least one parameter of the interference pattern, in particular direction and spatial frequency of the interference fringes in the one dimension or in both dimensions, by adjusting the direction and gradient of an inclination of the partial light beams of the selected pair of partial light beams.

By means of a beam path for guiding each pair of superposed partial light beams, configured to this end, at least the two desired point light sources of the same wavelength are ultimately produced on the respective pupil plane of the at least one eye of the user. In this context, the beam path for guiding each pair of superposed partial light beams can typically be configured so that at least the two interference patterns are each imaged on the retina, that is to say the light-sensitive layer, of the at least one eye of the user.

In a typical configuration of the present apparatus, a common inclination can be applied to at least both pairs of the partial light beams in addition to the inclination of the partial light beams of at least one pair, in particular in order to separate modulated light from non-modulated light, each of which are guided out of the at least one digital light modulation element. To this end, an optical axis of the at least one digital light modulation element can typically be aligned such that non-modulated light can be removed from the light beam by means of at least one filter which is configured to remove non-modulated light from the light beam following the passage thereof through the at least one digital light modulation element. To this end, the at least one filter may typically have or comprise at least one aperture stop. The term "aperture stop" in this context denotes an optical element which has an opening, typically an adjustable opening, through which a light beam or a part thereof may enter and thus pass the stop.

In a further typical configuration of the present apparatus, at least one beam-expanding, collimating optical element may be arranged between the at least one coherent light source and the at least one digital light modulation element. The at least one beam-expanding, collimating optical element may in this case typically comprise at least one diffuser, at least one optical lens, or at least one beam splitter. In this case, a "diffuser" denotes an optical element configured to scatter light, in particular by means of diffuse reflection and/or light refraction. Use of the at least one beam-expanding, collimating optical element may in particular allow a reduction in visibility of speckle patterns, which are produced by the coherent light. In particular, this may increase a measurement accuracy in the case of low contrasts.

In principle, the at least one digital light modulation element may be introduced at any location of the apparatus where it is sufficiently illuminated by the at least one expanded, collimated beam. In a special configuration, the at least one digital light modulation element can typically be introduced into a plane of an intermediate image. In this configuration, the at least one digital light modulation element can act as an intensity modulator, between crossed polarizers.

The compact and robustly constructed apparatus proposed herein consequently easily allows a production of isoluminant and monochromatic or polychromatic interference patterns, in particular in the form of interference fringes in one dimension or in two dimensions. On account of using the at least one digital light modulation element, a variable representation of different interference patterns, in particular, is rendered possible in the process. A wavefront is thus able to be resolved in spectrally different regions on the respective pupil plane when at least one supercontinuum laser source and at least one tunable wavelength filter are used. Advantageously, this allows the stimulus to be controlled in the input pupil and not in the intermediate image. This can enable an overlap in two conjugate pupils. For further details, reference is made to the exemplary embodiments.

In a further aspect, the present disclosure relates to an apparatus for determining a neural transfer function of a visual pathway of a user. In this context, the apparatus for determining a neural transfer function of the visual pathway of the user comprises at least one apparatus, as described in more detail above or below, for producing at least two point light sources of the same wavelength on a pupil plane of at least one eye of a user and an evaluation unit which is configured to determine a neural transfer function of the visual pathway of the user from the interference patterns that are imaged on the retina of the at least one eye of the user. In this way, the neural transfer function can be determined for any desired wavelength, for the entire visible spectrum, or for a part thereof.

In this context, the evaluation unit may be configured to produce information from at least one objective reaction of the user to the interference patterns imaged on the retina of the at least one eye of the user, wherein the reaction may be conscious or typically unconscious, wherein the neural transfer function of the visual pathway of the user can be determined from the information produced thus. As an alternative or in addition, the apparatus may further comprise an input unit that may be configured to register a psychophysical reaction of the user to the interference patterns imaged on the retina of the at least one eye of the user and to forward the reaction to the evaluation unit. To this end, use can be made of psychophysical algorithms that are based on regular correlations between a subjective mental experience of the user and at least one quantitatively measurable, objective physical stimulus in the form of the interference patterns imaged on the respective retina of the at least one eye of the user as a trigger for the experience of the user. In this case, the input unit may comprise any device by means of which subjective feedback by the user can be obtained, for example in the form of a manual, acoustic, or tactile input. The input unit can be a keyboard, in particular a keyboard with keys which the user can operate, typically press. As an alternative or in addition, this can typically be a virtual keyboard represented on a touch-sensitive visual display unit (touchscreen) of a mobile communications device, the user likewise being able to operate, typically press, the virtual keyboard. By operating the input unit, the user can consequently produce a measurement signal by means of the input unit, the measurement signal being able to be transmitted to the evaluation unit.

Typically, a mobile communications device should be understood to mean an apparatus which comprises at least one programmable processor and at least one camera and at least one acceleration sensor, and which is typically designed to be carried, that is to say configured in respect of dimensions and weight so that a person is capable of carrying it along. Further components can be present in the at least one mobile communications device, for example at least one visual display unit, at least one light source for, e.g., visible light from a wavelength range of 380 nm to 780 nm and/or infrared light from a wavelength range of 780 nm to 1 mm and/or at least one light receiver with a sensitivity to, e.g., visible light from a wavelength range from 380 nm to 780 nm and/or infrared light from a wavelength range from >780 nm to 1 mm. Typical examples of such mobile communications devices are smartphones or tablet PCs, which may comprise at least one visual display unit, for example at least one touch-sensitive visual display unit (touchscreen), at least one camera, at least one accelerometer, at least one light source, at least one light receiver and further components such as wireless interfaces for mobile radio or WLAN (wireless LAN).

In a further aspect, the present disclosure relates to a method for producing at least two point light sources of the same wavelength on a pupil plane of at least one eye of a user. The method comprises the following steps, typically in the specified order, with a partially or fully simultaneous implementation of the method steps being possible. It is furthermore possible for individual, multiple or all steps of the method to be performed repeatedly, in particular more than once. In addition to the stated method steps, the method may also comprise further method steps.

The method for producing at least two point light sources of the same wavelength on a pupil plane of at least one eye of a user comprising the steps:
 a) producing at least one light beam by means of at least one coherent light source;
 b) splitting the at least one light beam into two pairs of partial light beams respectively, superposing the respective partial light beams in each pair, and adjusting contrast and spatial phase in an interference pattern formed for each pair from the superposition of the two partial light beams; and
 c) guiding each pair of superposed partial light beams such that at least two point light sources of the same wavelength are produced on a pupil plane, or on the respective pupil plane, of at least one eye of a user, wherein at least one digital light modulation element is used to carry out step b).

According to method step a), there is a production of at least one light beam by means of at least one coherent light source.

According to method step b), there is a splitting of the at least one light beam into two pairs of partial light beams respectively, a superposing of the respective partial light beams in each pair, and an adjusting of contrast and spatial phase in an interference pattern formed for each pair from the superposition of the two partial light beams, for the purposes of which at least one digital light modulation element is used according to the disclosure.

According to method step c), there finally is a guiding of each pair of superposed partial light beams such that the at least two desired point light sources of the same wavelength are produced on the respective pupil plane of the at least one eye of the user.

In a particularly typical configuration, each pair of the superposed partial light beams is guided in accordance with step c) in such a way that the two interference patterns, especially the respective interference fringes in one dimension or in two dimensions, are each imaged on the respective retina of the at least one eye of the user.

In a further aspect, the present disclosure relates to a method for determining a neural transfer function of a visual pathway of a user. The method for determining a neural transfer function of the visual pathway of the user comprises steps a) to c) in accordance with the method for producing at least two point light sources of the same wavelength on a pupil plane, or on the respective pupil plane, of at least one eye of a user, and additionally a step d):
 d) determining a neural transfer function of the visual pathway of the user from the interference patterns which are imaged on the respective retina of the at least one eye of the user.

In a particularly typical configuration in this context, step d) may comprise a registering of a psychophysical reaction of the user to the interference patterns imaged on the respective retina of the at least one eye of the user. Especially in order to determine a meaningful psychometric function, it may be particularly advantageous to carry out at least step d) multiple times, even if steps a) to c) are only carried out once.

For further details in relation to the present methods, reference is made to the rest of the description relating to the apparatus.

In a further aspect, the present disclosure in each case relates to
 a computer program for producing at least two point light sources of the same wavelength on a pupil plane, or on the respective pupil plane, of at least one eye of a user, and
 a computer program for determining a neural transfer function of a visual pathway of a user,
wherein the respective computer program is configured to carry out associated steps a) to c) or a) to d), respectively, of the relevant method.

For further details in relation to the present computer programs, reference is made to the rest of the description relating to the methods and the apparatuses.

The apparatus according to the disclosure and the present methods have numerous advantages over conventional apparatuses and methods. The apparatuses have a compact and robust structure, and thus allow simple operation in order to be able to be used in a commercial product, for example in a clinical environment. These advantages are based in particular on the use of at least one digital light modulation element, typically at least one spatial light modulator or at least one digital micromirror unit, and thus avoid a complicated, complex and failure-prone combination comprising a rotating cube or a rotating prism. In this way, the desired determination of the neural transfer function of the visual pathway of the user can be implemented typically over the entire optical spectrum.

In summary, in the context of the present disclosure, the exemplary embodiments of the following clauses are particularly typical:

Clause 1. An apparatus for producing two point light sources of the same wavelength on a pupil plane of at least one eye of a user, comprising
- a coherent light source for producing a light beam;
- an optical device for splitting the light beam into two pairs of partial light beams, for superposing the respective partial light beams in each pair, and for adjusting contrast and spatial phase in an interference pattern formed for each pair from the superposition of the two partial light beams, wherein the optical device comprises a digital light modulation element; and
- a beam path for guiding each pair of superposed partial light beams such that two point light sources of the same wavelength are produced on a pupil plane of at least one eye of a user.

Clause 2. The apparatus according to the preceding clause, wherein the beam path for guiding each pair of superposed partial light beams is further configured for imaging the two interference patterns each on the retina of the at least one eye of the user.

Clause 3. The apparatus according to either of the preceding clauses, wherein the digital light modulation element is selected from a spatial light modulator (SLM) or a digital micromirror device (DMD).

Clause 4. The apparatus according to any one of the preceding clauses, wherein the digital light modulation element is configured to implement a lateral displacement of the partial light beams of one of the pairs of partial light beams in relation to a propagation direction of the partial light beams of the other pair of partial light beams.

Clause 5. The apparatus according to any one of the preceding clauses, wherein the digital light modulation element is configured to carry out any desired adjustment of the contrast in the interference pattern formed for each pair.

Clause 6. The apparatus according to the preceding clause, wherein the digital light modulation element is configured to carry out an isoluminant adjustment of the contrast in the interference pattern formed for each pair.

Clause 7. The apparatus according to any one of the preceding clauses, wherein the interference pattern is selected from interference fringes in one dimension or from interference fringes in two dimensions, wherein the interference fringes in two dimensions comprise a two-dimensional pattern selected from a checkerboard pattern, from alternating structures, and/or from attenuating structures.

Clause 8. The apparatus according to any one of the preceding clauses, furthermore comprising at least one optical filter which is configured to remove non-modulated light from the light beam following the passage through the digital light modulation element.

Clause 9. The apparatus according to the preceding clause, wherein the optical filter is or comprises an aperture stop.

Clause 10. The apparatus according to any one of the preceding clauses, wherein a beam-expanding, collimating optical system is arranged between the coherent light source and the digital light modulation element.

Clause 11. The apparatus according to the preceding clause, wherein the beam-expanding, collimating optical system comprises a diffuser.

Clause 12. The apparatus according to any one of the preceding clauses, wherein the apparatus is configured for generating two point light sources at respectively at least two mutually different wavelengths on the pupil plane of the at least one eye of the user.

Clause 13. The apparatus according to the preceding clause, wherein the apparatus is configured to produce in each case two point light sources at two or three mutually different wavelengths on the pupil plane of the at least one eye of the user.

Clause 14. The apparatus according to any one of the preceding clauses, wherein the coherent light source comprises a monochromatic light source.

Clause 15. The apparatus according to any one of the preceding clauses, wherein the coherent light source comprises a polychromatic light source and at least one wavelength filter.

Clause 16. The apparatus according to the preceding clause, wherein the polychromatic light source is or comprises a supercontinuum laser source.

Clause 17. An apparatus for determining a neural transfer function of a visual pathway of a user, comprising
- an apparatus for producing two point light sources of the same wavelength on a pupil plane of at least one eye of a user according to any one of the preceding clauses, and
- an evaluation unit for determining a neural transfer function of the visual pathway of the user from the interference patterns which are imaged on the retina of the at least one eye of the user.

Clause 18. The apparatus according to the preceding clause, further comprising an input unit which is configured to register a psychophysical reaction of the user to the interference patterns imaged on the retina of the at least one eye of the user and to forward the reaction to the evaluation unit.

Clause 19. The apparatus according to the preceding clause, wherein the input unit is selected from at least one keyboard, a virtual keyboard depicted on a touch-sensitive visual display unit of a mobile communications device, a microphone or a tactile sensor.

Clause 20. A method for producing two point light sources of the same wavelength on a pupil plane of at least one eye of a user comprises the steps:
a) producing a light beam by means of a coherent light source;
b) splitting the light beam into two pairs of partial light beams, superposing the respective partial light beams in each pair, and adjusting contrast and spatial phase in an interference pattern formed for each pair from the superposition of the two partial light beams,
wherein a digital light modulation element is used to carry out step b); and
c) guiding each pair of superposed partial light beams such that two point light sources of the same wavelength are produced on a pupil plane of at least one eye of a user.

Clause 21. The method according to the preceding clause, wherein the guiding of each pair of superposed partial light beams in accordance with step c) is implemented in such a way that the two interference patterns are each imaged on the retina of the at least one eye of the user.

Clause 22. The method according to any one of the two preceding clauses, wherein the method is carried out by means of an apparatus for producing two point light sources of the same wavelength on a pupil plane of the at least one eye of a user according to one of the preceding clauses relating to this apparatus.

Clause 23. A method for determining a neural transfer function of a visual pathway of a user, comprising steps a) to c) of the method for producing two point light sources of the same wavelength on a pupil plane of at least one eye of a user according to any one of the three preceding clauses, and additionally the subsequent step d):

d) determining a neural transfer function of the visual pathway of the user from the interference patterns which are imaged on the retina of the at least one eye of the user.

Clause 24. The method according to the preceding clause, wherein step d) comprises a registering of a psychophysical reaction of the user to the interference patterns imaged on the retina of the at least one eye of the user.

Clause 25. The method according to either of the two preceding clauses, wherein at least step d) is carried out multiple times.

Clause 26. A computer program for producing two point light sources of the same wavelength on a pupil plane of at least one eye of a user, wherein the computer program is configured to carry out the steps of the method for producing two point light sources of the same wavelength on a pupil plane of at least one eye of a user according to any one of the preceding clauses relating to this method.

Clause 27. A computer program for determining a neural transfer function of a visual pathway of a user, wherein the computer program is configured to carry out the steps of the method for determining a neural transfer function of the visual pathway of a user according to any one of the preceding clauses relating to this method.

Further details and features of the disclosure will become apparent from the following description of exemplary embodiments, in particular in conjunction with the dependent claims. In this case, the respective features can be realized by themselves or as a plurality in combination with one another. The disclosure is not restricted to the exemplary embodiments. The exemplary embodiments are illustrated schematically in the drawings. In this case, identical reference numerals in the individual drawings designate identical or functionally identical elements or elements corresponding to one another with regard to their functions.

BRIEF DESCRIPTION OF THE DRAWINGS

The disclosure will now be described with reference to the drawings wherein.

DESCRIPTION OF EXEMPLARY EMBODIMENTS

Figure 1:
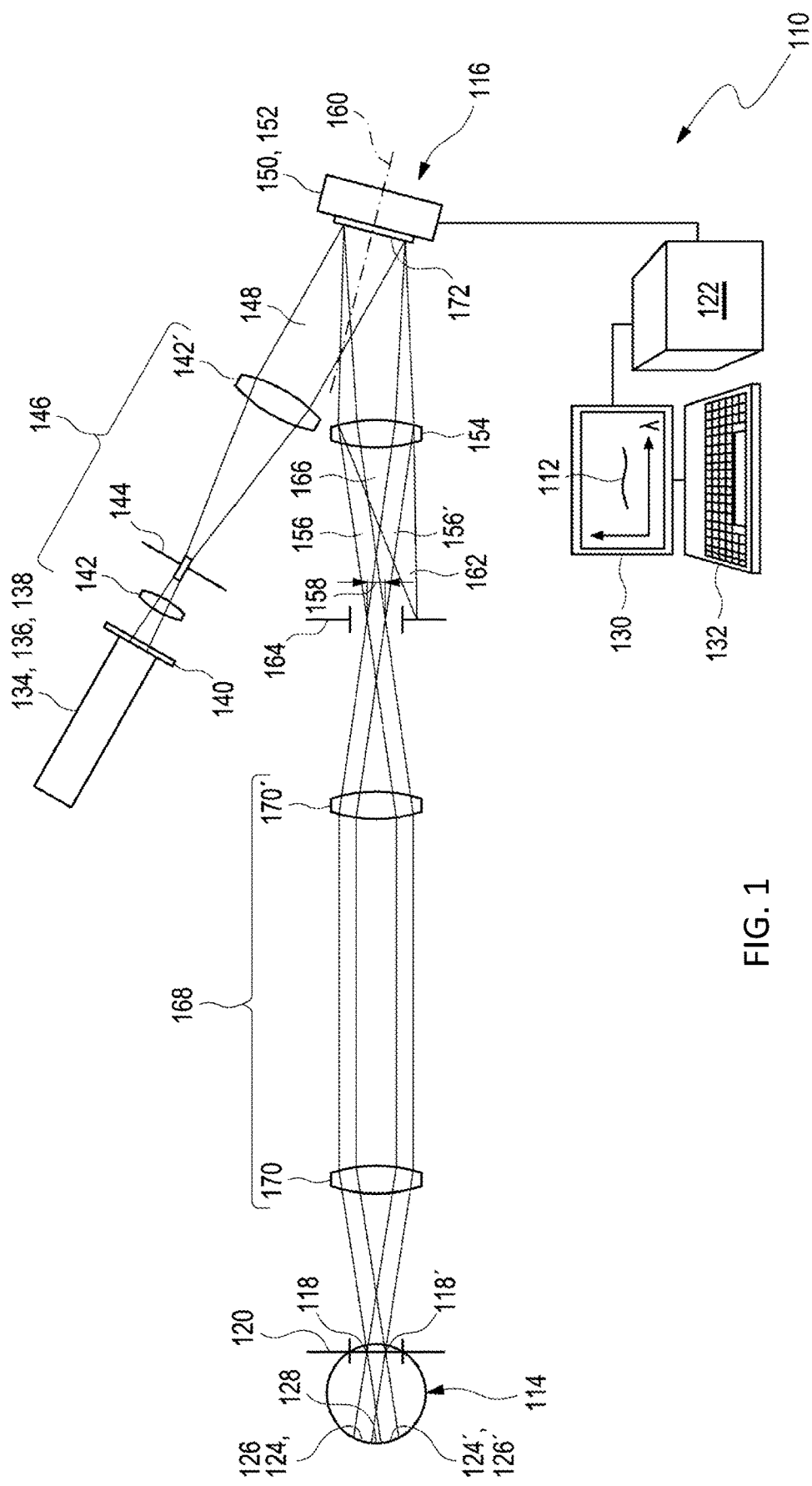
FIG. 1 shows a schematic illustration of an exemplary embodiment of an apparatus for determining a neural transfer function of a visual pathway of a user.

FIG. 1 shows a schematic illustration of an exemplary embodiment of an apparatus 110 for determining a neural transfer function 112 of a visual pathway of a user. In this case, the visual pathway denotes a chain of organs of the user configured to enable the user to see, with the chain of organs comprising at least an eye 114, retina, optic nerve and all centers in the brain that contribute to vision. The apparatus 110 for determining the neural transfer function 112 of the visual pathway of the user comprises an apparatus 116 for producing two point light sources 118, 118' of the same wavelength on a pupil plane 120 of the eye 114 of the user and an evaluation unit 122 which is configured to determine the neural transfer function 112 of the visual pathway of the user from interference patterns 124, 124', wherein the interference patterns 124, 124' are present in the form of checkerboard patterns 126, 126' in particular, which are imaged on the retina 128, that is to say on the light-sensitive layer, of the eye 114 of the user. In this case, the evaluation unit 122 can be configured to produce information from at least one objective, conscious or typically unconscious reaction of the user to the interference patterns 124, 124', wherein the neural transfer function 112 of the visual pathway of the user can be determined from information. Alternatively or in addition, the apparatus 110 may further comprise an input unit (not depicted here), which may be configured to register a psychophysical reaction of the user to the interference patterns 124, 124' and to transmit this reaction to the evaluation unit 122. In this context, the input unit may be selected from at least one keyboard, a virtual keyboard depicted on a touch-sensitive visual display unit (touchscreen) of a mobile communications device, a microphone or a tactile sensor. However, other types of input unit are possible.

As shown in FIG. 1, a monitor 130 can be used to display the neural transfer function 112 of the visual pathway of the user and a keyboard 132 can be used to control both the monitor 130 and the evaluation unit 122. As an alternative or in addition, the display of the neural transfer function 112 of the visual pathway of the user and/or the control of the evaluation unit 122 can be implemented by means of a mobile communications device (not depicted here), in particular by means of a smartphone or a tablet. However, other types of mobile communications device are possible. In a further alternative, the mobile communications device itself can be configured as the evaluation unit 122.

The apparatus 116 for producing the two point light sources 118, 118' of the same wavelength on the pupil plane 120 of the eye 114 of the user comprises a coherent light source 134, which may be present, in particular, in the form of a monochromatic light source (not depicted here), which provides coherent light within a narrowband range, or as a tunable polychromatic light source 136. The polychromatic light source may typically comprise a supercontinuum laser source 138 which is capable of providing coherent laser light at a plurality of wavelengths, with a tunable wavelength filter 140 being used to select a narrowband range from the broadband range. The combination of the supercontinuum laser source 138 and the tunable wavelength filter 140 enables a fast determination of the neural transfer function 112 over the entire visible spectrum or a part thereof.

The exemplary embodiment of the apparatus 116 for producing the two point light sources 118, 118' of the same wavelength on the pupil plane 120 of the eye 114 of the user, depicted schematically in FIG. 1, furthermore comprises a diffuser 144 arranged between two optical lenses 142, 142' which, together, as a beam-expanding, collimating optical element 146 ensure that the light beam 148 provided by the coherent light source 134 is expanded and collimated before it impinges on a digital light modulation element 150. In particular, the diffuser 144 renders possible a reduction in the visibility of speckle patterns produced by the coherent light, typically in order to increase a measurement accuracy in the case of low contrasts.

The expanded and collimated light beam 148 consequently impinges on the digital light modulation element 150 furthermore comprised by the apparatus 116 for producing the two point light sources 118, 118' of the same wavelength on the pupil plane 120 of the eye 114 of the user. The digital light modulation element 148 used in the exemplary embodiment according to FIG. 1 is designed as a spatial light modulator 152 (abbreviated "SLM") which is configured to electronically and/or optically impress an intensity pattern, in particular in the form of a spatial modulation and/or a phase, on the incident light beam. In an alternative, the digital light modulation element 150 may also be designed as a digital micromirror device (abbreviated "DMD"; not depicted here).

The digital light modulation element 150, assisted by an optical lens 154 in the present exemplary embodiment, is configured according to the disclosure to split the expanded and collimated light beam 148 into two pairs of partial light beams 156, 156', in such a way that the respective partial light beams 156, 156' in each pair are superposed on one another so that the interference patterns 124, 124' provided for imaging on the retina 128 are formed. In this case, the digital light modulation element 150 can advantageously be configured, at the same time, to adjust contrast and spatial phase in the interference patterns 124, 124' formed for each pair from the superposition of the two partial light beams 156, 156'. As FIG. 1 also shows, the digital light modulation element 150 may be configured to implement a lateral displacement 158 of the propagation direction of a first pair of partial light beams 156 in relation to the propagation direction of the other pair of partial light beams 156'. As a result, the digital light modulation element 150 is able to split the incident light beam 148 into two pairs of partial light beams 156, 156' that are inclined symmetrically with respect to one another. With regards to further details in this respect, reference is made to the description of FIGS. 2A and 3. To control the digital light modulation element 150, in particular to adjust the contrast and the spatial phase in the interference patterns 124, 124', use can be made of a separate control unit or, as depicted schematically in FIG. 1, use can be made of the aforementioned evaluation unit 122.

As is furthermore evident from FIG. 1, the digital light modulation element 150 may further be configured to split the incident light beam 148 in such a way that the two pairs of partial light beams 156, 156' have a common inclination (3. In this exemplary embodiment, an optical axis 160 of the digital light modulation element 150 may be aligned in such a way that light 162 which is incident on the digital light modulation element 150 but not modulated by the digital light modulation element 150 is able to be removed from the light beam 166, which is formed following the passage through the digital light modulation element 150, by means of an optical filter, typically by means of an aperture stop 164.

In an exemplary embodiment, a computer unit (not depicted here) can be used, the latter comprising the evaluation unit 122, the monitor 130, and the keyboard 132 and being able to be configured to control the digital light modulation element 150 and produce the interference patterns 124, 124' on the retina 128 of the eye 114 of the user. In this case, the same computer unit can additionally be configured to record optical measurement signals and/or to record subjective psychophysical signals, which may be produced from a reaction of the user, and/or to determine the neural transfer function 112. As an alternative or in addition, one or more individual computer units can be used to this end.

As also shown in FIG. 1, each pair of superposed partial light beams 156, 156' is guided in the direction of the eye 114 of the user by means of a beam path 168, which is configured to this end and which comprises two further optical lenses 170, 170', in such a way that, ultimately, the two desired point light sources 118, 118' of the same wavelength are produced on the pupil plane 120 of the eye 114 of the user. In the exemplary embodiment according to FIG. 1, the beam path 168 is configured such that the two interference patterns 124, 124' are both imaged on the retina 128 of the eye 114 of the user.

Figure 2A:
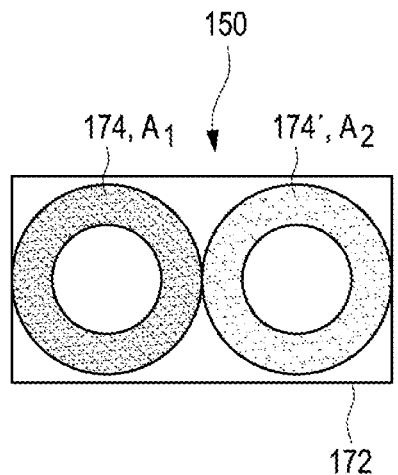
FIGS. 2A and 2B show a schematic illustration of an adjustment of a contrast in interference patterns by means of a digital light modulation element.
Figure 2B:
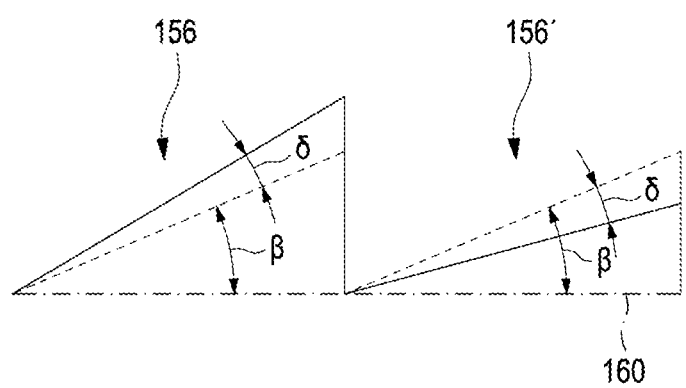

FIGS. 2A and 2B show a schematic illustration of the adjustment of the contrast in the interference patterns 124, 124' by means of the digital light modulation element 150.

To this end, FIG. 2A schematically depicts rings 174, 174' assigned to the respective pair of partial light beams 156, 156' and on a plane 172 of the digital light modulation element 150. In this context, a ratio of the areas $A_1:A_2$ of the rings 174, 174' can enable an adjustment of the contrast of the associated interference pattern 124, 124', in particular of the associated checkerboard patterns 126, 126', on the retina 128 of the eye 114 of the user. By way of example, an isoluminant setting of the contrast of 100% in the interference patterns 124, 124' can be implemented by setting the ratio of the areas $A_1:A_2=1:1$. Then again, a contrast of 25% can be produced by setting the ratio of the areas $A_1:A_2=4:1$ or $A_1:A_2=1:4$, while a contrast of 0% can be produced by setting the ratio of the areas $A_1:A_2=1:0$ or $A_1:A_2=0:1$. Further examples are possible. In particular, such a procedure can allow contrast changes in the interference patterns 124, 124' to be carried out at a high repetition rate, which is only restricted by the repetition rate of the digital light modulation element 150, while a luminance of the two partial light beams 156, 156' can be kept constant at the same time.

FIG. 2B shows a schematic illustration of inclinations of the light beam 166 which forms after the passage through the digital light modulation element 150, vis-à-vis the optical axis 160 of the digital light modulation element 150. In addition to a common inclination β, which both pairs of the partial light beams 156, 156' have, each of the partial light beams 156, 156' may have an individual inclination δ, δ' as a consequence of the areas $A_1, A_2$ of the rings 174, 174' on the plane 172 of the digital light modulation element 150.

The apparatus 116 for producing the two point light sources 118, 118' of the same wavelength on the pupil plane 120 of the eye 114 of the user consequently allows the generation of isoluminant monochromatic interference patterns 124, 124', which may be present as checkerboard patterns 126, 126' in particular. To produce polychromatic interference patterns (not depicted here), in particular polychromatic checkerboard patterns, use can be made of the aforementioned tunable polychromatic light source 136, in particular the supercontinuum laser source 138, in combination with the tunable wavelength filter 140, in order in each case to select a narrowband range assigned to a certain color from the provided coherent laser light of a plurality of wavelengths, in order thereby to resolve a wavefront into spectrally different regions on the pupil plane 120.

In the process, it is possible to select two individual narrowband ranges, for example from the green and the red spectral range. In this way, it is possible to produce four rings (not depicted here) on the plane 172 of the digital light modulation element 150, with a respective pair for each color. An adjustment in the relative positions of the green and the red interference patterns 124, 124' can be enabled by introducing a constant phase shift into that part of the digital light modulation element 150 which corresponds to a spatial frequency determining the colors on the associated inclination δ, δ'.

Figure 3:
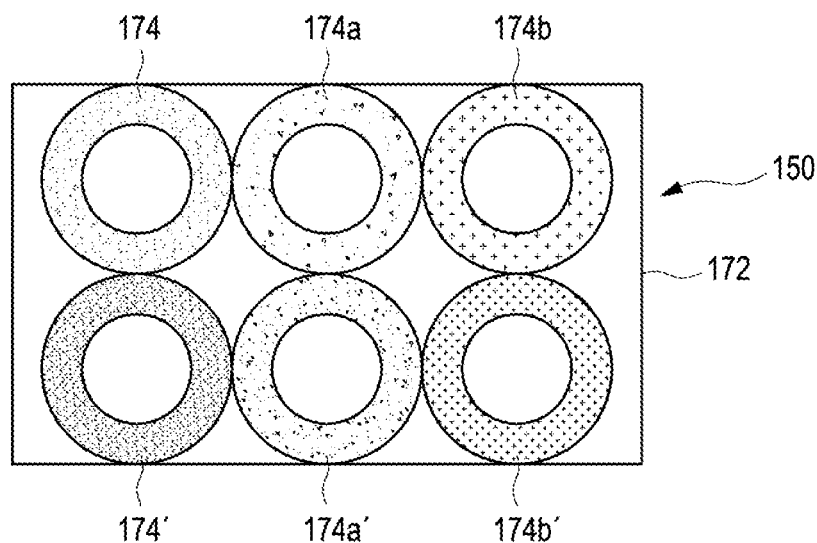
FIG. 3 shows a schematic illustration of the adjustment of the digital light modulation element for producing a polychromatic interference pattern.

FIG. 3 shows a schematic illustration of the adjustment of the digital light modulation element for producing a polychromatic interference pattern for three individual narrowband ranges, for example from the blue, the green, and the red spectral range. In this way, it is possible to produce six rings 174, 174', 174a, 174a', 174b, 174b' on the plane 172 of the digital light modulation element 150, in each case one pair for each color, with each pair corresponding to its wavelength. In this case, the associated inclination δ, δ', δ" (not depicted here) can typically be determined individually for each pair since the respective phase shift depends on the relevant wavelength, in order to produce respective interference fringes in the checkerboard patterns 126, 126' with the same period. In this way, it is possible to produce a stable polychromatic interference pattern which is imaged on the retina.

Figure 4:
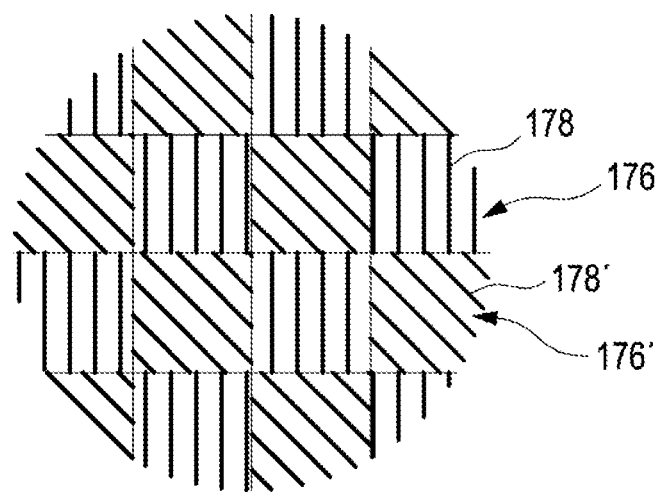
FIG. 4 shows a schematic illustration of particularly typical interference patterns.

FIG. 4 shows a schematic illustration of an exemplary embodiment of the interference patterns 124, 124' which are provided for imaging on the retina 128 and which, as depicted here, are present in the form of the checkerboard pattern 126 with first regions 176 and second regions 176'. In this case, each of the two regions 176, 176' comprises interference fringes 178, 178' in each case, with the two regions 176, 176' differing from one another in terms of the respective inclination δ, δ' of the interference fringes 178, 178'. This type of interference patterns 124, 124' can typically be produced by means of a phase mask on the digital light modulation element 150, in particular on the spatial light modulator 152, especially by combining two masked pupils in the form of the checkerboard pattern 126 with two simultaneously applied inclinations δ, δ' of the interference fringes 178, 178'. However, further exemplary embodiments of the interference patterns 124, 124' provided for imaging on the retina 128 are conceivable.

Figure 5:
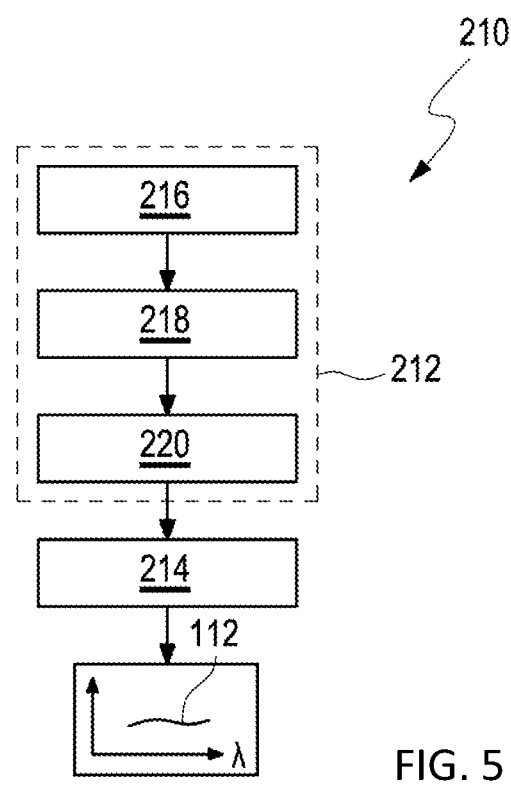
FIG. 5 shows a flowchart of an exemplary embodiment of a method for determining the neural transfer function of a visual pathway of a user.

FIG. 5 shows a flowchart of an exemplary embodiment of a method 210 for determining the neural transfer function 112 of the visual pathway of a user.

The method 210 for determining the neural transfer function 112 of the visual pathway of the user in this case comprises a method 212 for producing the two point light sources 118, 118' of the same wavelength on the pupil plane 120 of the eye 114 of the user and a determination step 214 in accordance with step d) for determining the neural transfer function 112 of the visual pathway of the user from the interference patterns 124, 124', in particular the checkerboard patterns 126, 126' which are schematically depicted in FIG. 4 and which may have first regions 176 and second regions 176', which each comprise interference fringes 178, 178' with different inclinations δ, δ', which are imaged on the retina 128 of the eye 114 of the user.

To produce the interference patterns 124, 124', in particular the checkerboard patterns 126, 126', which are imaged on the retina 128 of the eye 114 of the user, there is in an illumination step 216 in accordance with step a) a production of the light beam 148 by means of the coherent light source 134, typically by means of the tunable polychromatic light source 136, in particular the supercontinuum laser source 138;

in a modulation step 218 using the digital light modulation element 150, in particular the spatial light modulator 152, in accordance with step b) a splitting of the light beam 148 into two pairs of partial light beams 156, 156', a superposing of the respective partial light beams 156, 156' in each pair, and an adjusting of contrast and spatial phase in an interference pattern 124, 124' formed for each pair from the superposition of the two partial light beams 156, 156'; and in an impingement step 220 in accordance with step c) a guiding of each pair of the superposed partial light beams 156, 156' such that the two point light sources 118, 118' of the same wavelength are produced on the pupil plane 120 of the eye 114 of a user in such a way that the two interference patterns 124, 124' are in each case imaged on the retina 128 of the eye 114 of the user.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

110 Apparatus for determining the neural transfer function of a visual pathway of a user
112 Neural transfer function
114 Eye
116 Apparatus for producing the two point light sources of the same wavelength on the pupil plane of at least one eye of a user
118, 118' Point light source
120 Pupil plane
122 Evaluation unit
124, 124' Interference pattern
126, 126' Checkerboard pattern
128 Retina
130 Monitor
132 Keyboard
134 Coherent light source
136 Polychromatic light source
138 Supercontinuum laser source
140 Tunable wavelength filter
142, 142' Optical lens
144 Diffuser
146 Beam-expanding, collimating optical element
148 Light beam 150 Digital light modulation element
152 Spatial light modulator
154 Optical lens
156, 156' Pair of partial light beams
158 Lateral displacement
160 Optical axis
162 Non-modulated light
164 Aperture stop
166 Light beam
168 Beam path
170, 170' Further optical lenses
172 Plane (of the digital light modulation element)
174, 174' Ring
176, 176' Region
178, 178' Interference fringes
210 Method for determining a neural transfer function of a visual pathway of a user
212 Method for producing two point light sources of the same wavelength on a pupil plane of at least one eye of a user
214 Determination step
216 Illumination step
218 Modulation stop
220 Impingement step

The invention claimed is:

1. An apparatus for producing at least two point light sources of a same wavelength on a pupil plane of at least one eye of a user, the apparatus comprising:
at least one coherent light source configured to produce at least one light beam;
at least one optical device configured to split the at least one light beam into two pairs of partial light beams, respectively, to superpose the respective partial light beams in each pair, and to adjust a contrast and a spatial phase in an interference pattern formed for each pair from the superposition of the two partial light beams, wherein the at least one optical device includes at least one digital light modulation element, and wherein the digital light modulation element is an optical apparatus that includes a multiplicity of individually controllable optical elements, which are configured to modulate the incident light beam; and
at least one beam path configured to guide each pair of superposed partial light beams such that the at least two point light sources of the same wavelength are produced on a respective pupil plane of the at least one eye of the user,
wherein the at least one coherent light source includes at least one polychromatic light source with a supercontinuum laser source and at least one tunable wavelength filter.

2. The apparatus as claimed in claim 1, wherein the at least one beam path for guiding each pair of superposed partial light beams is further configured to image the at least two interference patterns each on a respective retina of the at least one eye of the user.

3. The apparatus as claimed in claim 1, wherein the at least one digital light modulation element is selected from at least one spatial light modulator or at least one digital micromirror device.

4. The apparatus as claimed in claim 1, wherein the at least one digital light modulation element is configured to implement at least one lateral displacement of the partial light beams of at least one of the pairs of partial light beams in relation to a propagation direction of the partial light beams of at least one other pair of partial light beams.

5. The apparatus as claimed in claim 1, wherein the at least one digital light modulation element is configured to carry out any desired adjustment of the contrast in the interference pattern formed for each pair.

6. The apparatus as claimed in claim 1, further comprising:
at least one optical filter which is configured to remove non-modulated light from the light beam following a passage through the at least one digital light modulation element.

7. The apparatus as claimed in claim 1, wherein at least one beam-expanding, collimating optical system is arranged between the at least one coherent light source and the at least one digital light modulation element.

8. The apparatus as claimed in claim 1, wherein the apparatus is configured to generate at least two point light sources, respectively each having a different wavelength from each other on the respective pupil plane of the at least one eye of the user.

9. A method for producing at least two point light sources of a same wavelength on a respective pupil plane of at least one eye of a user, the method comprising the following steps:
a) producing at least one light beam with at least one coherent light source;
b) splitting the at least one light beam into two pairs of partial light beams, respectively, superposing the respective partial light beams in each pair, and adjusting a contrast and a spatial phase in an interference pattern formed for each pair from the superposition of the two partial light beams with at least one digital light modulation element, wherein the digital light modulation element is an optical apparatus that includes a multiplicity of individually controllable optical elements, which are configured to modulate the incident light beam; and
c) guiding each pair of superposed partial light beams such that at least two point light sources of the same wavelength are produced on a respective pupil plane of the at least one eye of the user,
wherein the at least one light beam is produced by the at least one coherent light source with at least one polychromatic light source containing a supercontinuum laser source and at least one tunable wavelength filter.

10. The method as claimed in claim 9, wherein the guiding of each pair of superposed partial light beams in accordance with step c) is implemented such that the two interference patterns are each imaged on the respective retina of the at least one eye of the user.

11. A computer program for producing at least two point light sources of a same wavelength on the respective pupil plane of at least one eye of a user, the computer program being stored on a non-transitory storage medium and comprising commands which, when the program is executed by a computer, prompt the latter to carry out the following steps:
a) producing at least one light beam with at least one coherent light source;
b) splitting the at least one light beam into two pairs of partial light beams, superposing the respective partial light beams, respectively, and adjusting a contrast and a spatial phase in an interference pattern formed for each pair from the superposition of the two partial light beams with at least one digital light modulation element, wherein the digital light modulation element is an optical apparatus that includes a multiplicity of individually controllable optical elements, which are configured to modulate the incident light beam; and c) guiding each pair of superposed partial light beams such that at least two point light sources of the same wavelength are produced on the respective pupil plane of the at least one eye of the user, wherein the at least one light beam is produced by the at least one coherent light source with at least one polychromatic light source containing a supercontinuum laser source and at least one tunable wavelength filter.

\* \* \* \* \*